United States Patent [19]

Toda et al.

[11] Patent Number: 5,100,904
[45] Date of Patent: Mar. 31, 1992

[54] PROLINAL COMPOUNDS WHICH ARE USEFUL IN TREATING AMNESIA

[75] Inventors: Masaaki Toda, Osaka; Shuichi Ohuchida, Kyoto; Hiroyuki Ohno, Shiga, all of Japan

[73] Assignee: Ono Pharmaceutical Co., Ltd., Osaka, Japan

[21] Appl. No.: 533,648

[22] Filed: Jun. 5, 1990

Related U.S. Application Data

[62] Division of Ser. No. 123,410, Nov. 20, 1987, Pat. No. 4,956,380.

[30] Foreign Application Priority Data

Nov. 20, 1986 [JP] Japan .................. 61-275375
Sep. 14, 1987 [JP] Japan .................. 62-228452

[51] Int. Cl.$^5$ ................ A61K 31/44; C07D 215/18
[52] U.S. Cl. ................... 514/343; 546/103; 546/104; 546/105; 546/106; 546/108; 546/110; 546/141; 546/143; 546/146; 546/153; 546/157; 546/159; 546/162; 546/164; 546/165; 546/166; 546/171; 546/175; 546/281; 514/297; 514/298; 514/307; 514/309; 514/310; 514/312; 514/313; 514/314
[58] Field of Search ........... 546/275, 103, 104, 105, 546/106, 108, 110, 141, 143, 146, 153, 157, 159, 162, 164, 165, 166, 171, 172, 281; 514/343, 297, 298, 307, 309, 310, 312, 313, 314

[56] References Cited
FOREIGN PATENT DOCUMENTS 0080822 12/1990 European Pat. Off. ........... 548/517

OTHER PUBLICATIONS

Chemical Abstracts, vol. 105, No. 23, Abstract 209,396q, pp. 643–644, Dec. 8, 1986.

Primary Examiner—C. Warren Ivy
Assistant Examiner—Zinna Northington-Davis
Attorney, Agent, or Firm—Sughrue, Mion, Zinn, Macpeak & Seas

[57] ABSTRACT

A novel prolinal derivatives of the general formula:

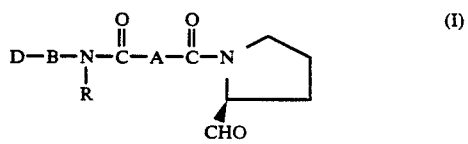

[wherein
A represents alkylene or alkenylene group of from 1 to 8 carbon atom(s) or a saturated hydrocarbon ring of from 3 to 7 carbon atoms,
R represents hydrogen atom, phenyl group, benzyl group, alkyl group of from 1 to 8 carbon atom(s) or cycloalkyl group of from 3 to 7 carbon atoms,
B represents alkylene group of from 1 to 8 atom(s) unsubstituted or substituted by phenyl group or benzyl group, or a single bond,
D represents carbocyclic or heterocyclic ring unsubstituted or substituted by from one to three of halogen atom, alkyl or alkoxy group of from 1 to 4 carbon atom(s), nitro group or trifluoromethyl group.]

possess inhibitory activity on prolyl endopeptidase, and therefore are useful for treating and/or preventing agent as a amnesia.

6 Claims, No Drawings

PROLINAL COMPOUNDS WHICH ARE USEFUL IN TREATING AMNESIA

This is a divisional of application Ser. No. 07/123,410 filed Nov. 20, 1987 now U.S. Pat. No. 4,956,380.

SUMMARY

This invention is related to novel compounds having an inhibitory activity on prolyl endopeptidase.

More particularly, this invention is related to:

1) Novel prolinal derivatives having an inhibitory activity on prolyl endopeptidase, of the following general formula:

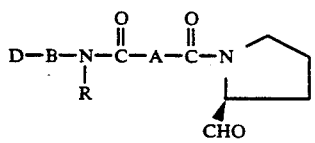

(I)

wherein all of the symbols are the same meaning as hereafter defined.

2) process for the preparation of them, and 3) anti-amnesia agents containing them as an active ingredient.

BACKGROUND

Recent advance in neuroscience is making clear the natural shape of neurotransmitters, substances deeply related to memory in the brain. It is said that some of these substances are neuropeptides containing prolines.

Recovery of the memory was reported by the dose of neuropeptide containing proline to an experimental amnesia rat (See Science 211, 601 (1981)).

On the other hand, it is presumed that these neuropeptide-hormones shall be metabolized by cerebral endogenous peptidases. Especially, prolyl endopeptidase (EC, 3. 4. 21. 26) might take part in this metabolism closely (See J. Biochem., 94, 1179 (1983)).

From these facts, studies were in progress that it should be possible to prevent or treat amnesia by inhibiting prolyl endopeptidase and suppressing the metabolism of neutrotransmitters. (See Protein, Nucleic acid and Enzyme 25(6), 513(1980); Nippon Nougei Kagaku Kaishi 58(11), 1147(1984); J. Neurochem., 41, 69(1983); ibid 42, 237(1984).)

For the purpose described above, several compounds were synthesized. For example, it is clear that N-benzyloxycarbonyl-glycyl-L-prolyl-chloromethane and N-benzyloxycarbonyl-L-prolyl-prolinal strongly inhibit prolyl endopeptidase (See J. Neurochem., 41, 69 (1983)). More recently, it is disclosed that compounds shown below are effective for the above purpose.

(i) Prolinal derivatives of general formula:

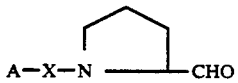

(A)

wherein A represents a protecting group of an amino acid group in the field of amino acid chemicals, and X represents a residual group of an amino acid.

See Japanese Patent Kokai No. 60-188317, i.e. European Patent Publication No. 154353.

(ii) N-acylpyrrolidine derivatives of general formula:

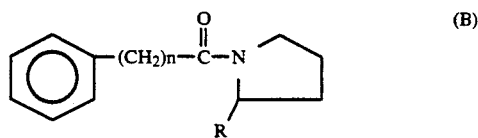

(B)

wherein n represents a number of 1–4, and R represents an lower alkyl ester group, —CH$_2$OH group or aldelyde group.

See Japanese Patent Kokai No. 61-37764;. a compound wherein n is 5 is also disclosed by correction, i.e. European Patent Publication No. 172458.

(iii) Compounds of general formula:

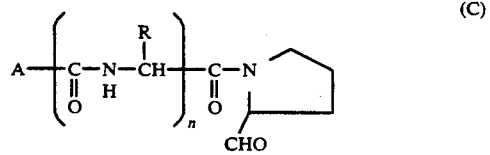

(C)

wherein A represents a methyl group or benzyloxy group, R represents an isopropyl group, or isobutyl group on the condition that plural R's are of the same meaning in one formula. And n represents 2 or 3.

See Japanese Patent Kokai No. 61-183297.

Most recently, five applications related to anti-amnesia agents having prolinal skeltons were published.

(iv) Compounds of general formula:

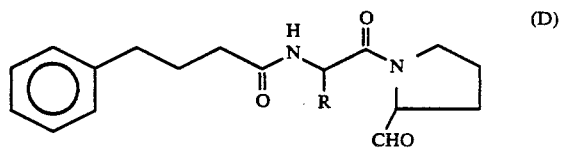

(D)

wherein R represents a group of —CH$_3$,

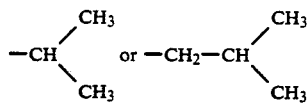

See Japanese Patent Kokai No. 61-238775, i.e. European Patent Publication No. 201741.

(v) N-acylpyrrolidine derivatives of general formula:

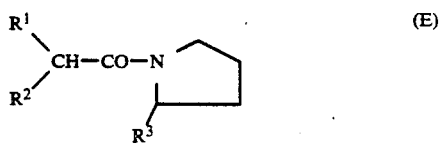

(E)

wherein R$^3$ represents a lower alkyloxycarbonyl group, hydroxymethyl group or formyl group, R$^1$ represents a hydrogen atom or lower alkyl group, R$^2$ represents a· phenyl group or a group of the following general formula:

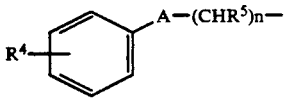

wherein R⁴ represents a hydrogen atom, a halogen atom or lower alkoxy group, R⁵ represents a hydrogen atom or lower alkyl group, n represents 0 or 1, A represents an oxygen atom, methylene group, hydroxymethylene group, phenylmethylene group or carbonyl group; or R¹ and R² represent, together a, benzylidene group unsubstituted or substituted by aromatic ring(s).

See Japanese Patent Kokai No. 61-238776, i.e. European Patent Publication No. 201742.

(vi) Compounds of general formula:

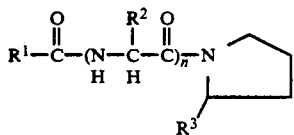

wherein n represents a number of 0~2, R¹ represents a straight-chained organic group of from 5 to 25 carbon atoms which is saturated or unsaturated wherein a, unsaturated carbon chain may contain a plural number of double bonds, R² represents a group of

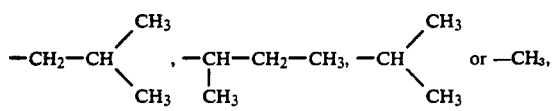

R³ represents a lower alkyl ester group, —CH₂OH group or aldelyde group.

See Japanese Patent Kokai No. 61-238799, i.e. European Patent Publication No. 201743.

(vii) Compounds of general formula:

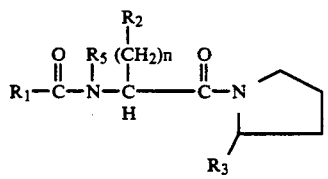

wherein n is an integer of more than one, R₁ is a saturated or unsaturated straight-chained hydrocarbon group of from 5 to 25 carbon atoms wherein an, unsaturated carbon chain may contain a plural number of double bonds, R³ represents a lower alkyl ester group of the formula: —COOR⁴ (wherein R⁴ represents a lower alkyl group), hydroxymethyl group or formyl group, R² represents a methyl group, phenyl group, hydroxyphenyl group, indolyl group, imidazolyl group, carboxyl group, formyl group, amino group, hydroxy group, hydroxyalkyl group, thiol group, methylthio group or guanidino group, etc., and each of the above groups may be substituted and R⁵ represents a hydrogen atom or a single bond between a carbon atom and nitrogen atom together with R² when n is 3.

See Japanese Patent Kokai No. 62-84058, i.e. European Patent Publication No. 201743.

(viii) Dipeptide derivatives of general formula:

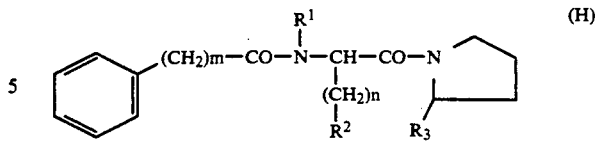

wherein m represents an integer of 1~8, n represents an integer of 1~6, R¹ represents a hydrogen atom, R² represents a hydrogen atom, a branched alkyl group of from 3 to 5 carbon atoms, phenyl group, hydroxyphenyl group, indolyl group, imidazolyl group or methylthio group, or a single bond between a carbon atom and nitrogen atom together with R² and R³ repesents a lower alkyl ester group, hydroxymethyl group or formyl group.

See Japanese Patent Kokai No. 62-148467, i.e. European Patent Publication No. 201741.

COMPARISON WITH THE PRIOR ART

The compounds of the present invention of the general formula (I) are prolyl endopeptidase inhibitors having the same prolinal (i.e. pyrrolidin-2-al) skelton as compounds of the general formulae of from (A) to (H) and compounds shown in the literature, i.e. J. Neurochem., 41.

But, the compounds of the present invention are novel and different compounds from the compounds cited hereinbefore in structure.

That is to say, the compounds shown in (B) and (E) have structures that a phenylalkanoyl, phenoxyalkanoyl or benzoylalkanoyl group is attached to the nitrogen atom of prolinal. And the compounds shown in (A), (C), (D), (F), (G) and (H) have structures that amino acid is combined to the nitrogen atom of prolinal.

Compared with the above compounds, the compounds of the present invention have the structure wherein the group represented by D and the prolinal were linked with dicarboxylic acid, i.e. the structural feature of the compounds of the present invention is the presence of peptide-bond in the reverse.

DISCLOSURE OF THE INVENTION

The present invention is related to:
1) novel prolinal derivative of the general formula:

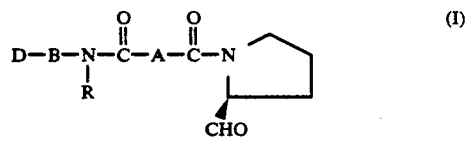

wherein
A represents an alkylene or alkenylene group of from 1 to 8 carbon atom(s) or a saturated hydrocarbon ring of from 3 to 7 carbon atoms, R represents a hydrogen atom, phenyl group, benzyl group, alkyl group of from 1 to 8 carbon atom(s) or cycloalkyl group of from 3 to 7 carbon atoms,
B represents an alkylene group of from 1 to 8 atom(s) unsubstituted or substituted by a phenyl group or benzyl group or a single bond, D represents a carbocyclic or heterocyclic ring unsubstituted or substituted by from one to three of a halogen atom, alkyl or alkoxy group of from 1 to 4 carbon atom(s), nitro group or trifluoromethyl group, 2) Processes for the preparation of them and
3) Anti-amnesia agents containing them as an active ingredient.

In the general formula (I), alkylene group of from 1 to 8 carbon atom(s) represented by A or B means methylene, ethylene, trimethylene, tetramethylene, pentamethylene, hexamethylene, heptamethylene and octamethylene groups and isomeric groups thereof. Alkenylene groups of from 2 to 8 carbon atoms means group described above but not a methylene group wherein optional double bound(s) is or are contained.

In the above groups, groups of from 1 to 4 carbon atom(s) are preferred.

In the general formula (I), saturated hydrocarbon ring of from 3 to 7 carbon atoms represented by A means cyclopropane, cyclobutane, cyclopentane, cyclohexane and cycloheptane rings.

In the general formula (I), alkyl group of from 1 to 8 carbon atom(s) represented by R means methyl, ethyl, propyl, butyl, pentyl, hexyl, heptyl and octyl groups and isomeric groups thereof. Cycloalkyl group of from 3 to 7 carbon atoms represented by R means cyclopropyl, cyclobutyl, cyclopentyl, cyclohexyl and cycloheptyl groups.

In the general formula (I), carbocyclic ring represented by D means mono-, bi- or tri-cyclic aromatic carbocyclic ring(s) containing not more than 15 carbon atoms which may be partially or fully saturated.

Examples of the rings mentioned above are benzene, naphthalene, indene, azulene, fluorene, phenanthrene, anthracene, acenaphthalene, biphenylene rings and partially or fully saturated rings thereof.

In the general formula (I), heterocyclic ring represented by D means mono-, bi- or tri-aromatic heterocyclic ring(s) containing not more than 15 carbon and hetero atoms which may be partially or fully saturated. In the above heterocyclic rings, rings containing one or two of hetero atom(s) are preferred.

Examples of the rings mentioned above are furan, thiophene, pyrrole, oxazole, isoxazole, thiazole, isothiazole, imidazole, pyrazole, furazan, pyran, pyridine, pyridazine, pyrimidine, pyrazine, indole, isoindole, benzofuran, benzothiophene, indolizine, chromene, quinoline, isoquinoline, quinolizine, purine, indazole, quinazoline, cinnoline, quinozaline, phthalazine, pteridine, carbazole, acridine, phenanthridine, xanthene, phenazine, phenothiazine rings and partially or fully saturated rings thereof.

In the general formula (I), preferred rings represented by D especially are benzene, napthalene, fluorene, pyridine, furan and acridine rings and partially saturated rings thereof.

In the above rings, substituted benzene rings are preferred as substituted rings by substituent(s).

In the general formula (I), in D, halogen atom means fluorine, chlorine, bromine and iodine atoms. Alkyl group of from 1 to 4 carbon atom(s) means methyl, ethyl, propyl and butyl groups and isomeric groups thereof, and alkoxy group of from 1 to 4 carbon atom(s) means methoxy, ethoxy, propoxy and butoxy groups and isomeric groups thereof.

Throughout the specification including claims, stereo isomers generated by stereo configuration(s) (asymmetric carbon, double bond etc.) and structural isomers generated by branching of a carbon chain etc., are included in the present invention.

For example, it may be easily understood that alkylene and alkenylene groups include straight-chained and also branched-chained ones, to the skilled in the art.

Rings represented by A or rings in D may be attached to the adjoined group at any position.

PROCESS FOR THE PREPARATION

According to the present invention, the compounds of the present invention of the general formula (I) may be prepared by oxidizing a compound of general formula:

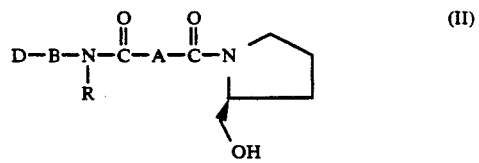

wherein all of the symbols are the same meaning as hereinbefore defined, in a mild condition.

Oxidation in a mild condition is known and may be carried out, for example, using an oxidation agent (sulfur trioxide-pyridine complex, chromium trioxide-pyridine complex, t-butyl chloroformate, oxalyl chloride etc.), with a tertiary amine (triethylamine, pyridine etc.) or without, in an inert organic solvent (DMSO, methylene chloride, chloroform, benzene etc.), at a temperature of from 0° C. to 50° C.

PROCESS FOR THE PREPARATION OF INTERMEDIATES

Prolinol derivatives of the general formula (II) may be prepared by reacting prolinol of the formula:

and an acid of general formula:

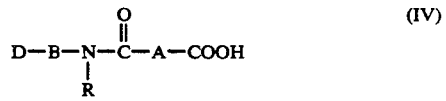

wherein all of the symbols are the same meaning as hereinbefore defined, to form an amide bond.

Reaction to form an amide bond with a carboxylic acid and a secondary amine is known, and it may be carried out, for example, by (1) a mixed acid anhydride method, e.g. using an acid halide (pivaloyl chloride etc.) or an acid derivative (ethyl chloroformate, isobutyl chloroformate etc.), in the presence of a tertiary amine (triethylamine etc.), in an inert organic solvent (THF, methylene chloride, chloroform, ethyl ether etc.), at a temperature of from 0° C. to 50° C.), or (2) using an activating agent such as DCC, e.g. using DCC, with a tertiary amine or without, in an inert organic solvent (THF, methylene chloride, chloroform, ethyl ether etc.), at a temperature of from 0° C. to 50° C.

The acid of the general formula (IV) may be prepared by the following series of reactions shown in the scheme [A].

Scheme [A]

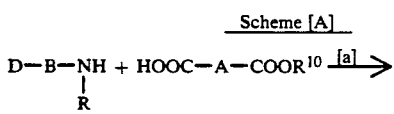

(V)   (VI)

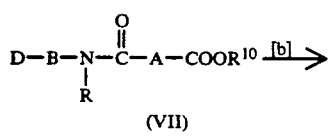

(VII)

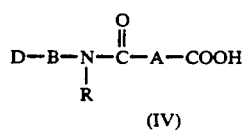

(IV)

Each symbol in the reaction scheme [A] represents the following meanings or is the same as hereinbefore defined.

$R^{10}$: alkyl group of from 1 to 4 carbon atom(s)

In the scheme [A], each reaction step is known per se, and summarized descriptions are the following.

Step [a] is a reaction to form an amide bond with a carboxylic acid and an amine, and it may be carried out, for example, using the same procedure as the step to react the compound of the general formula (II) and the compound of the general formula (III), described before, or (3) using an acid halide. The acid halide method is known, and it may be carried out, for example, reacting an acid halide (thionyl chloride, oxalyl chloride etc.) and a compound of the general formula (VI), and the resulting acid halide, which is corresponding to the acid of the general formula (VI), is reacted with an amine of the general formula (V), in the presence of a tertiary amine (pyridine, triethylamine etc.), in an inert organic solvent (THF, methylene chloride etc.).

Step [b] is saponification, and is a known reaction, and it may be carried out, for example, using an aqueous solution of an alkali (sodium hydroxide, potassium hydroxide etc.), in an alkanol (ethanol, methanol etc.).

The compounds of the general formula (III), (V) and (VI) are known per se or may be prepared by known methods.

Throughout the specification, in each reaction, products may be purified by conventional methods, for example, distillation at atmospheric or reduced pressure, high performance liquid chromatography, thin layer chromatography using silica gel or magnesium silicate or washing or recrystallization. Purification may be carried out after each reaction or a series of reactions.

PHARMACOLOGICAL ACTIVITIES

The compounds of the present invention of the general formula (I) possess an inhibitory activity on prolyl endopeptidase, described before. For example, in a standard laboratory test, results in the following are given.

Prolyl endopeptidase inhibitory activity in vitro

The compounds of the present invention showed activities as in the following Table I, with the test system described hereafter.

TABLE I

| Example No. of the compounds | Concentration for 50% inhibition $IC_{50}$ (μM) |
|---|---|
| 1 | 0.13 |
| 1 (a) | 0.23 |
| 1 (h) | 0.07 |
| 1 (s) | 1.9 |
| 1 (x) | 0.014 |
| 1 (bb) | 1.2 |
| 2 (a) | 0.023 |
| 2 (e) | 0.16 |
| 2 (n) | 0.0019 |
| 2 (y) | 0.043 |
| 2 (dd) | 0.79 |

Inhibitory activity of prolyl endopeptidase was measured by the following test system.

A mixed solution of 20 mM tris-HCl buffer (pH 7.5; 935 μl; containing 10 mM EDTA and 10 mM mercaptoethanol), a solution of a compound of the present invention in DMSO (10 μl) and a solution of prolyl endopeptidase which was purified from bovine brain (0.13 unit; prepared by the method described in J. Biochem., 94, 1179 (1983)) in tris-HCl buffer (15 μl) was preincubated for 15 mins at 37° C.

To the solution, 5 mM of N-benzyloxycarbonyl-glycyl-prolyl-p-nitroanilide (40 μl) in a mixture of 40% dioxane—60% water was added. The solution was incubated for 1 min at the same temperature.

Optical absorption ($a_1$) at 405 nm of the solution, and optical absorption ($a_2$) at 405 nm of the solution after more 30 mins' incubation at 37° C. were measured.

Optical absorptions ($b_1$ and $b_2$) of the solutions using DMSO instead of the solution of the compound of the present invention were also measured.

Inhibitory ratio was calculated by the following expression and $IC_{50}$ (required concentration for 50% inhibition) was obtained (See Protein, Nucleic acid and Enzyme 25(6), 513, 1980.).

$$\text{Inhibitory ratio } (\%) = \frac{(b_2 - b_1) - (a_2 - a_1)}{b_2 - b_1} \times 100$$

Toxicity

On the other hand, it was confirmed that the acute toxicity ($LD_{50}$) of the compounds of the present invention was more than 500 mg/kg animal body weight by intravenous administration. Therefore, the prolinal derivatives of the present invention may be considered to be sufficiently safe and suitable for pharmaceutical used.

APPLICATION FOR THE PHARMACEUTICALS

To inhibit prolyl endopeptidase is to suppress the metabolism of neurotransmitters, substances taking part in memory in brain described hereinbefore, and therefore be useful for prevention and/or treatment of amnesia, in animals including human beings, especially human beings.

The compounds of the present invention possess a inhibitory activity on prolyl endopeptidase in vitro, so they are expected to be useful for prevention and/or treatment of amnesia.

For the purpose above described, the compounds of the present invention may normally by administered systemically or partially, usually by oral or parenteral administration.

The doses to be administered are determined depending upon age, body weight, symptom, the desired therapeutic effect, the route of administration, and the duration of the treatment, etc. In the human adult, the doses per person per dose are generally between 1 mg and 500 mg, by oral administration, up to several times per day, and between 1 mg and 100 mg, by parenteral administration, up to several times per day.

As mentioned above, the doses to be used depend upon various conditions. Therefore, there are cases in which doses lower than or greater than the ranges specified above may be used.

Solid compositions for oral administration include compressed tablets, pills, dispersible powders, capsules, and granules. In such compositions, one or more of the active compound(s) is or are admixed with at least one inert diluent (lactose, mannitol, glucose, hydroxypropylcellulose, microcrystalline cellulose, starch, polyvinylpyrrolidone, magnesium metasilicate alminate, etc.). The compositions may also comprise, as is normal practice, additional substances other than inert diluents: e.g. lubricating agents (magnesium stearate etc.), disintegrating agents (cellulose calcium gluconate, etc.), assisting agents for dissolving (glutamic acid, aspartic acid, etc.) and stabilizing agents (lactose, etc.).

The tablets or pills may, if desired, be coated with gastric or enteric material (sugar, gelatin, hydroxypropylcellulose or hydroxypropylmethyl cellulose phthalate, etc.).

Capsules include soft ones and hard ones.

Liquid compositions for oral administration include pharmaceutically-acceptable emulsions, solutions, suspensions, syrups and elixirs.

In such compositions, one or more of the active compound(s) is or are used with an inert diluent(s) commonly used in the art (purified water, ethanol etc.).

Besides inert diluents, such compositions may also comprise adjuvants (wetting agents, suspending agents, etc.), sweetening agents, flavouring agents, perfuming agents and preserving agents.

Other compositions for oral administration include spray compositions which may be prepared by known methods and which comprise one or more of the active compound(s).

Spray compositions may comprise additional substances other than inert diluents: e.g. stabilizing agents (sodium sulfite, etc.) and isotonic buffers (sodium chloride, sodium citrate, citric acid, etc.).

For preparation of such spray compositions, for example, the method described in the U.S. Pat. Nos. 2,868,691 or 3,095,355 may be used.

Injections for parenteral administration include sterile aqueous or non-aqueous solutions, suspensions and emulsions. In such compositions, one or more of active compound(s) is or are admixed with at least one of inert aqueous diluent(s) (distilled water for injection, physiological salt solution, etc.) or inert non-aqueous diluent(s) (propylene glycol, polyethylene glycol, olive oil, ethanol, POLYSOLBATE 80 (registered trade mark), etc.).

Injections may comprise other than inert diluents: e.g. preserving agents, wetting agents, emulsifying agents, dispersing agents, stabilizing agents (lactose, etc.), assisting agents such as assisting agents for dissolving (glutamic acid, aspartic acid, etc.).

They may be sterilized, for example, by filtration through a bacteria-retaining filter, by incorporation of sterilizing agents in the compositions or by irradiation. They also be manufactured in the form of sterile solid compositions, for example, by freeze-drying, and which can be dissolved in sterile water or some other sterile diluents for injection immediately before use.

Other compositions for parenteral administration include liquids for external use, and endermic liniments (ointment, etc.), suppositories and pessaries which comprise one or more of the active compound(s) and may be prepared by known methods.

REFERENCE EXAMPLES AND EXAMPLES

The following reference examples and examples illustrate the present invention, but not limit the present invention.

The solvents in the parentheses show the developing or eluting solvents and the ratios of the solvents used are by a volume in chromatographic separations.

Unless otherwise specified, "IR" were measured by liquid film method.

REFERENCE EXAMPLE 1

Synthesis of N-[3-[N-(2-phenylethyl)carbamoyl]-propanoyl]-L-prolinol

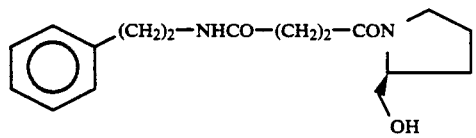

3-[N-(2-phenylethyl)carbamoyl]propionic acid (400 mg) was dissolved into dry THF (4 ml). Triethylamine (0.32 ml) and ethyl chloroformate (0.15 ml) secondary were dropped into the solution with stirring at 0° C. After 10 mins' stirring, a solution of L-prolinol (199 mg) in THF (2 ml) was added to the solution, and the solution was stirred for 30 mins at 0° C. and for another 30 mins at room temperature. Water was added to the diluted solution with ethyl acetate. The oily layer was washed with 1N hydrochloric acid, a saturated aqueous solution of sodium hydrocarbonate, a saturated brine, successively, dried and then evaporated. The residue was purified by column chromatography on silica gel to give the title compound (490 mg).

EXAMPLE 1

Synthesis of N-[3-[N-(2-phenylethyl)carbamoyl]-propanoyl]-L-prolinal

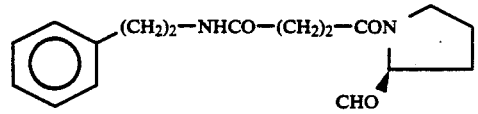

N-[3-[N-(2-phenylethyl)carbamoyl]propanoyl]-L-prolinol (490 mg; prepared in reference example 1) was dissolved in dry DMSO (5 ml). Triethylamine (0.79 ml) was added to the solution. A solution of sulfur trioxide-pyridine complex (450 mg) in DMSO (2 ml) was dropped to the solution. After 10 mins' stirring, the solution was poured into water. The mixture was extracted with ethyl acetate. The oily layer was washed with 1N hydrochloric acid, a saturated aqueous solution of sodium hydrocarbonate and a saturated brine, successively, dried and then evaporated. The residue was purified by column chromatography on silica gel to give the title compound (371 mg) having the following physical data:

TLC: Rf 0.22 (EtOAc: CH$_3$OH=19:1);
IR: ν3300, 2950–1900, 1715, 1600, 1530, 1420, 1050, 740, 690, 650 cm$^{-1}$.

EXAMPLE 1 (a)-1 (dd)

By the same procedures as reference example 1 and example 1, using each compounds depicted in the following reaction formulae, each compounds having the physical data shown in the Table II were given.

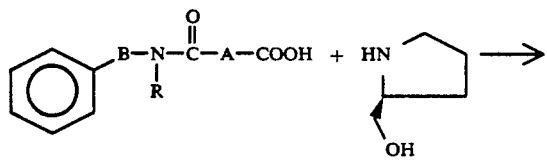

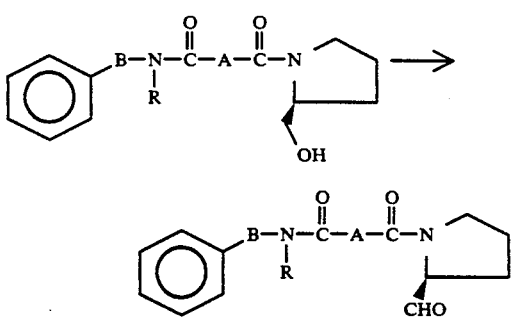

TABLE II

| No. | —B—NR—CO—A— | Name | TLC | IR (cm$^{-1}$) |
|---|---|---|---|---|
| 1 (a) | —CH$_2$—NHCO—(CH$_2$)$_2$— | N-[3-(N-benzylcarbamoyl)propanoyl]-L-prolinal | Rf 0.28 (EtOAc:CH$_3$OH = 19:1) | ν 3280, 1720, 1600, 1520, 1420, 1230, 1040, 730, 690 |
| 1 (b) | —CH$_2$—N(CH$_3$)—CO—(CH$_2$)$_2$— | N-[3-(N-benzyl-N-methylcarbamoyl)propanoyl]-L-prolinal | Rf 0.40 (EtOAc:CH$_3$OH = 19:1) | ν 1720, 1620, 1420, 1100, 1050, 730, 690 |
| 1 (c) | —CH$_2$—N(φ)—CO—(CH$_2$)$_2$— | N-[3-(N-benzyl-N-phenylcarbamoyl)propanoyl]-L-prolinal | Rf 0.27 (n-C$_6$H$_{14}$:EtOAc = 1:4) | ν 1720, 1630, 1585, 1480, 1390, 1250, 1070, 1005, 690 |
| 1 (d) | —CH$_2$—NHCO—(CH$_2$)$_3$— | N-[4-(N-benzylcarbamoyl)butanoyl]-L-prolinal | Rf 0.52 (EtOAc:CH$_3$OH = 9:1) | ν 3280, 1720, 1610, 1520, 1420, 1230, 1020, 690 |
| 1 (e) | —(CH$_2$)$_3$—NHCO—(CH$_2$)$_2$— | N-[3-[N-(3-phenylpropyl)carbamoyl]propanoyl]-L-prolinal | Rf 0.34 (EtOAc:CH$_3$OH = 9:1) | ν 3300, 2930, 1720, 1620, 1530, 1425, 745, 690 |
| 1 (f) | —(CH$_2$)$_4$—NHCO—(CH$_2$)$_2$— | N-[3-[N-(4-phenylbutyl)carbamoyl]propanoyl]-L-prolinal | Rf 0.39 (EtOAc:CH$_3$OH = 9:1) | ν 3300, 2920, 1720 |
| 1 (g) | —CH$_2$—NHCO—(CH$_2$)$_4$— | N-[5-(N-benzylcarbamoyl)pentanoyl]-L-prolinal | Rf 0.29 (EtOAc:CH$_3$OH = 19:1) | ν 3280, 1720, 1610, 1520, 1420, 1040, 730, 690 |
| 1 (h) | —(CH$_2$)$_5$—NHCO—(CH$_2$)$_2$— | N-[3-[N-(5-phenylpentyl)carbamoyl]propanoyl]-L-prolinal | Rf 0.36 (EtOAc:CH$_3$OH = 19:1) | ν 3300, 1720, 1610, 1530, 1430, 1040, 730, 690 |
| 1 (i) | —CH$_2$—NHCO—CH(iBu)—CH$_2$— | N-[3-(N-benzylcarbamoyl)-4-methylpentanoyl]-L-prolinal | Rf 0.26 (EtOAc) | ν 3300, 1725, 1640–1620, 1535, 1440 |
| 1 (j) | —CH(CH$_3$)—NHCO—(CH$_2$)$_2$— | N-[3-[N-(1S-phenylethyl)carbamoyl]propanoyl]-L-prolinal | Rf 0.35 (EtOAc:CH$_3$OH = 9:1) | ν (CHCl$_3$ solution) 3450, 2950, 1720, 1650–1620, 1490, 1430 |
| 1 (k) | —CH$_2$—N(t-Bu)—CO—(CH$_2$)$_2$— | N-[3-(N-benzyl-N-t-butylcarbamoyl)propanoyl]-L-prodinal | Rf 0.31 (EtOAc:n-C$_6$H$_{14}$ = 4:1) | ν 1720, 1620, 1390, 1180, 1010, 970, 740, 695 |
| 1 (l) | —CH$_2$—N(CH$_2$φ)—CO—(CH$_2$)$_2$— | N-[3-(N,N-dibenzylcarbamoyl)propanoyl]-L-prolinal | Rf 0.30 (EtOAc:n-C$_6$H$_{14}$ = 4:1) | ν 1720, 1620, 1420, 1190, 1070, 1010, 730, 690 |
| 1 (m) | —CH$_2$—N(iPr)—CO—(CH$_2$)$_2$— | N-[3-(N-benzyl-N-isopropylcarbamoyl)propanoyl]-L-prolinal | Rf 0.30 (EtOAc) | ν 1720, 1620, 1410, 1170, 1050, 720, 680 |
| 1 (n) | —CH$_2$—N(Et)—CO—(CH$_2$)$_2$— | N-[3-(N-benzyl-N-ethylcarbamoyl)propanoyl]-L-prolinal | Rf 0.16 (EtOAc) | ν 1720, 1620, 1410, 1240, 1110, 1070, 730, 690 |

TABLE II-continued

| No. | —B—NR—CO—A— | Name | TLC | IR (cm$^{-1}$) |
|---|---|---|---|---|
| 1 (o) | —(CH$_2$)—N(CH$_3$)—CO—(CH$_2$)$_2$— | N-[3-[N-methyl-N-(2-phenylethyl)carbamoyl]propanoyl]-L-prolinal | Rf 0.35 (EtOAc:CH$_3$OH = 19:1) | ν 1720, 1620, 1420, 1230, 1160, 1100, 1050, 740, 690 |
| 1 (p) | —CH$_2$—NHCO—CH$_2$—CH(iPr) | N-[2-(N-benzylcarbamoylmethyl)-3-methylbutanoyl]-L-Prolinal | Rf 0.36 (EtOAc) | ν 3300, 1725, 1610, 1540, 1440, 750, 695 |
| 1 (q) | —(CH$_2$)$_3$—NHCO—CH$_2$— | N-[N-(3-phenylpropylcarbamoyl)acetyl]-L-prolinal | Rf 0.18 (EtOAc) | ν (CHCl$_3$ solution) 1725, 1660 |
| 1 (r) | —CH$_2$—N[(CH$_2$)$_3$CH$_3$]—CO—(CH$_2$)$_2$— | N-[3-(N-n-butyl-N-benzylcarbamoyl)propanoyl]-L-prolinal | Rf 0.37 (EtOAc) | ν 1720, 1620, 1410, 1200, 720, 690 |
| 1 (s) | —CH$_2$—N(CH$_3$)—CO—CH=CH— | N-[3-(N-benzyl-N-methylcarbamoyl)acryloyl]-L-prolinal | Rf 0.40 (EtOAc:CH$_3$OH = 19:1) | ν 1720, 1600, 1410, 1090, 1050, 960, 750, 730, 690 |
| 1 (t) | —(CH$_2$)$_2$—N(CH$_2$φ)—CO—(CH$_2$)$_2$— | N-[3-[N-benzyl-N-(2-phenylethyl)carbamoyl]propanoyl]-L-prolinal | Rf 0.35 (EtOAc) | ν 1720, 1620, 1410, 1230, 1070, 1020, 730, 690 |
| 1 (u) | —CH$_2$—N(cyclopentyl)—CO—(CH$_2$)$_2$— | N-[3-(N-benzyl-N-cyclopentylcarbamoyl)propanoyl]-L-prolinal | Rf 0.36 (EtOAc) | ν 1720, 1620, 1410, 1170, 1070, 1010, 950, 720, 690 |
| 1 (v) | —CH$_2$—N(CH$_3$)—CO—(cyclopropyl)— | N-[2-(N-benzyl-N-methylcarbamoyl)cyclopropane-1-carbonyl]-L-prolinal | Rf 0.40 (EtOAc:CH$_3$OH = 19:1) | ν 1720, 1610, 1420, 1200, 1100, 725, 690 |
| 1 (w) | —CH$_2$—N(CH$_3$)—CO—(cyclohexyl)— | N-[2-(N-benzyl-N-methylcarbamoyl)cyclohexane-1-carbonyl]-L-prolinal | Rf 0.46 and 0.38 (EtOAc) | ν 1720, 1620, 1430, 1110, 730, 690 |
| 1 (x) | —CH$_2$—NH—CO—(cyclopentyl)— | N-[(1R,2R)-2-(N-benzylcarbamoyl)cyclopentane-1-carbonyl]-L-prolinal | Rf 0.41 (EtOAc) | ν 3300, 1720, 1610, 1520, 1420, 1230, 1020, 690 |
| 1 (y) | —CH$_2$—N(φ)—CO—(cyclopentyl)— | N-[(1R,2R)-2-(N-benzyl-N-phenylcarbamoyl)cyclopentane-1-carbonyl]-L-prolinal | Rf 0.44 (EtOAc:n-C$_6$H$_{14}$ = 4:1) | ν 1720, 1620, 1480, 1400, 1240, 1070, 1010, 690 |
| 1 (z) | —CH$_2$—N(CH$_3$)—CO—(cyclopentyl)— | N-[(1R,2R)-2-(N-benzyl-N-methylcarbamoyl)cyclopentane-1-carbonyl]-L-prolinal | Rf 0.26 (EtOAc:n-C$_6$H$_{14}$ = 4:1) | ν 1720, 1620, 1430, 1230, 1110, 730, 690 |
| 1 (aa) | —CH$_2$—CH(φ)—NHCO—(CH$_2$)$_2$— | N-[3-[N-(1,2-diphenylethyl)carbamoyl]propanoyl]-L-prolinal | Rf 0.40 (EtOAc:CH$_3$OH = 9:1) | ν (CHCl$_3$ solution) 3460, 3300, 3000, 1730, 1640, 1490, 1440, 690 |
| 1 (bb) | —CH(φ)—CH$_2$—NHCO—(CH$_2$)$_2$— | N-[3-[N-(2,2-diphenylethyl)carbamoyl]propanoyl]-L-prolinal | Rf 0.38 (EtOAc:CH$_3$OH = 9:1) | ν (CHCl$_3$ solution) 3460, 3000, 1730, 1650–1620, 1500, 1440, 690 |

TABLE II-continued

| No. | —B—NR—CO—A— | Name | TLC | IR (cm$^{-1}$) |
|---|---|---|---|---|
| 1 (cc) | —CH—NHCO—(CH$_2$)$_2$—<br>  \|<br>  φ | N-[3-(N-diphenylmethylcarbamoyl)<br>propanoyl]-L-prolinal | Rf 0.43<br>(EtOAc:CH$_3$OH =<br>19:1) | ν (KBr tablet)<br>3280, 1720, 1620,<br>1510, 1415, 1200,<br>1050. 730, 690 |
| 1 (dd) | —N—CO—(CH$_2$)$_2$—<br>  \|<br>  φ | N-[3-(N,N-diphenylcarbamoyl)<br>propanoyl]-L-prolinal | Rf 0.26<br>(EtOAc) | ν (CHCl$_3$ solution)<br>2980, 1720,<br>1650–1640, 1590,<br>1480, 1430, 1170,<br>1280, 680 |

EXAMPLE 2 (a)–2 (ee)

By the same procedure as reference example 1 and example 1, using each compounds depicted in the following reaction formulae, each compounds having the physical data shown in the Table III were given.

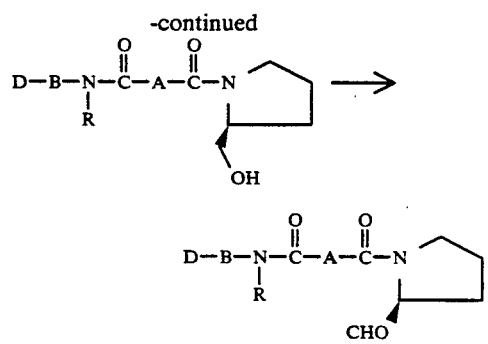

TABLE III

| No. | D—B—NR—CO—A— | Name | TLC | IR (cm$^{-1}$) |
|---|---|---|---|---|
| 2 (a) | 4-CH$_3$-C$_6$H$_4$-CH$_2$—NHCO—(CH$_2$)$_2$— | N-[3-[N-(4-methylbenzyl)-<br>carbamoyl]<br>propanoyl]-L-prolinal | Rf 0.40<br>(EtOAc:CH$_3$OH =<br>9:1) | ν 3300, 2950, 1720,<br>1650–1600, 1520,<br>1420, 790, 740 |
| 2 (b) | 3-OCH$_3$-C$_6$H$_4$-CH$_2$—NHCO—(CH$_2$)$_2$— | N-[3-[N-(3-methoxybenzyl)-<br>carbamoyl]<br>propanoyl]-L-prolinal | Rf 0.26<br>(EtOAc:CH$_3$OH =<br>9:1) | ν 3300, 2950, 1730,<br>1620, 1540, 1440,<br>1260, 1150, 1040,<br>790, 740, 690 |
| 2 (c) | 4-CH$_3$O-C$_6$H$_4$-CH$_2$—NHCO—(CH$_2$)$_2$— | N-[3-[N-(4-methoxybenzyl)-<br>carbamoyl]<br>propanoyl]-L-prolinal | Rf 0.36<br>(EtOAc:CH$_3$OH =<br>9:1) | ν 3300, 2930, 1720,<br>1640, 1610, 1500,<br>1430, 1240, 1165,<br>1020, 800, 740 |
| 2 (d) | 4-NO$_2$-C$_6$H$_4$-CH$_2$—NHCO—(CH$_2$)$_2$— | N-[3-[N-(4-nitrobenzyl)-<br>carbamoyl]<br>propanoyl]-L-prolinal | Rf 0.29<br>(EtOAc:CH$_3$OH =<br>9:1) | ν 3500–3300, 2930,<br>1730, 1620, 1510,<br>1440, 1340, 1250,<br>1150, 1040, 860,<br>740 |
| 2 (e) | 2-Cl-C$_6$H$_4$-CH$_2$—NHCO—(CH$_2$)$_2$— | N-[3-[N-(2-chlorobenzyl)-<br>carbamoyl]<br>propanoyl]-L-prolinal | Rf 0.44<br>(EtOAc:CH$_3$OH =<br>9:1) | ν 3300, 3150, 2900,<br>1730, 1600, 1540,<br>1440, 1270, 1045,<br>760 |
| 2 (f) | 4-Cl-C$_6$H$_4$-CH$_2$—NHCO—(CH$_2$)$_2$— | N-[3-[N-(4-chlorobenzyl)-<br>carbamoyl]<br>propanoyl]-L-prolinal | Rf 0.43<br>(EtOAc:CH$_3$OH =<br>9:1) | ν 3300, 2950, 1725,<br>1660–1600, 1530,<br>1490, 1430, 1090,<br>1010, 800, 750 |
| 2 (g) | 2-OCH$_3$-C$_6$H$_4$-CH$_2$—NHCO—(CH$_2$)$_2$— | N-[3-[N-(2-methoxybenzyl)-<br>carbamoyl]<br>propanoyl]-L-prolinal | Rf 0.25<br>(EtOAc:CH$_3$OH =<br>9:1) | ν 3300, 2940, 2840,<br>1725, 1620, 1530,<br>1490, 1430, 1240,<br>1120, 1030, 750 |

TABLE III-continued

| No. | D—B—NR—CO—A— | Name | TLC | IR (cm$^{-1}$) |
|---|---|---|---|---|
| 2 (h) | 3-chlorobenzyl-CH₂—NHCO—(CH₂)₂— | N-[3-[N-(3-chlorobenzyl)-carbamoyl]propanoyl]-L-prolinal | Rf 0.23 (EtOAc:CH₃OH = 9:1) | ν 3300, 3050, 2930, 1720, 1620, 1520, 1420, 1250, 1070, 1010, 770, 670 |
| 2 (i) | 2-fluorobenzyl-CH₂—NHCO—(CH₂)₂— | N-[3-[N-(2-fluorobenzyl)-carbamoyl]propanoyl]-L-prolinal | Rf 0.33 (EtOAc:CH₃OH = 19:1) | ν 3280, 3050, 1720, 1610, 1520, 1430, 1215, 1090, 820, 750 |
| 2 (j) | 4-chlorobenzyl-CH₂—NHCO—cyclopentane | N-[(1RS,2R)-2-[N-(4-chlorophenylmethyl)carbamoyl]cyclopentane-1-carbonyl]-L-prolinal | Rf 0.39 (EtOAc:CH₃OH = 95:5) | ν 3300, 2940, 1720, 1650-1600, 1520, 1480, 1420, 1080, 1000, 790, 750 |
| 2 (k) | 4-methylbenzyl-CH₂—NHCO—cyclopentane | N-[(1RS,2R)-2-[N-(4-methylphenylmethyl)carbamoyl]cyclopentane-1-carbonyl]-L-prolinal | Rf 0.40 (EtOAc:CH₃OH = 95:5) | ν 3290, 2930, 1720, 1650-1600, 1520, 1420, 740 |
| 2 (l) | 4-methylbenzyl-CH₂—N(CH₃)—CO—(CH₂)₂— | N-[3-[N-methyl-N-(4-methylphenylmethyl)carbamoyl]propanoyl]-L-prolinal | Rf 0.30 (CHCl₃:CH₃OH = 20:1) | ν 1725, 1630, 1430 |
| 2 (m) | 4-chlorobenzyl-CH₂—N(CH₃)—CO—(CH₂)₂— | N-[3-[N-(4-chlorophenylmethyl)-N-methylcarbamoyl]propanoyl]-L-prolinal | Rf 0.25 (EtOAc:CH₃OH = 19:1)) | ν 1720, 1620, 1485, 1430, 1090 |
| 2 (n) | 4-methylbenzyl-CH₂—N(Φ)—CO—(CH₂)₂— | N-[3-[N-(4-methylphenylmethyl)-N-phenylcarbamoyl]propanoyl]-L-prolinal | Rf 0.40 (EtOAc) | ν 1720, 1630, 1590, 1490, 1390, 1260, 1010, 695 |
| 2 (o) | 4-chlorobenzyl-CH₂—N(Φ)—CO—(CH₂)₂— | N-[3-[N-(4-chlorophenylmethyl)-N-phenylcarbamoyl]propanoyl]-L-prolinal | Rf 0.42 (EtOAc) | ν 1720, 1630, 1585, 1480, 1390, 1250, 1080, 1000, 690 |
| 2 (p) | 4-trifluoromethylbenzyl-CH₂—NHCO—(CH₂)₂— | N-[3-[N-(4-trifluoromethylphenylmethyl)carbamoyl]propanoyl]-L-prolinal | Rf 0.47 (EtOAc:CH₃OH = 19:1) | ν 3250, 1720, 1600, 1520, 1410, 1310, 1240, 1100, 1050, 800 |
| 2 (q) | 4-methoxybenzyl-CH₂—N(CH₃)—(CH₂)₂— | N-[3-[N-(4-methoxyphenylmethyl)-N-methylcarbamoyl]propanoyl]-L-prolinal | Rf 0.08 (EtOAc) | ν 1720, 1620, 1505, 1420, 1240, 1170, 1105, 1025 |
| 2 (r) | 2-chlorophenyl-(CH₂)₂—NHCO—(CH₂)₂— | N-[3-[N-[2-(2-chlorophenyl)ethyl]carbamoyl]propanoyl]-L-prolinal | Rf 0.33 (EtOAc:CH₃OH = 9:1) | ν 3300, 2950, 1720, 1620, 1330, 1245, 1040, 750 |
| 2 (s) | 4-methoxyphenyl-(CH₂)₂—NHCO—(CH₂)₂— | N-[3-[N-[2-(4-methoxyphenyl)ethyl]carbamoyl]propanoyl]-L-prolinal | Rf 0.32 (EtOAc:CH₃OH = 9:1) | ν 3300, 2900, 1720, 1610, 1310, 1425, 1240, 1020, 810 |

TABLE III-continued

| No. | D—B—NR—CO—A— | Name | TLC | IR (cm$^{-1}$) |
|---|---|---|---|---|
| 2 (t) | 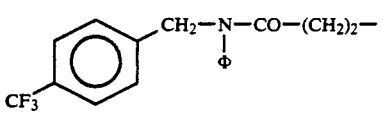 | N-[3-[N-phenyl-N-(4-trifluoromethylphenylmethyl)carbamoyl]propanoyl]-L-prolinal | Rf 0.34 (EtOAc) | ν 2950–2900, 1725, 1630, 1590, 1480, 1410, 1390, 1310, 1260, 1150, 1110, 1010, 690 |
| 2 (u) | 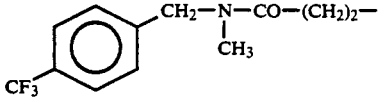 | N-[3-[N-methyl-N-(4-trifluoromethylphenylmethyl)carbamoyl]propanoyl]-L-prolinal | Rf 0.22 (EtOAc:CH$_3$OH = 95:5) | ν 2950–2800, 1725, 1630, 1430, 1410, 1320, 1150, 1110, 1060, 1010, 750 |
| 2 (v) | 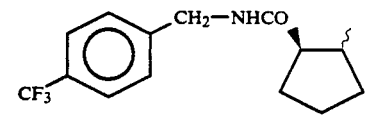 | N-[(1RS,2R)-2-[N-(4-trifluoromethylphenyl)carbamoyl]cyclopentane-1-carbonyl]-L-prolinal | Rf 0.45 (EtOAc) | ν 3300, 1720, 1610, 1520, 1430, 1320, 1150, 1110, 1060, 1010, 810 |
| 2 (w) | 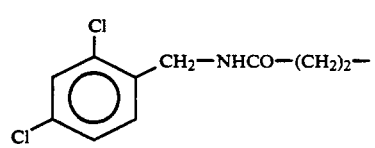 | N-[3-[N-(2,4-dichlorophenylmethyl)carbamoyl]-propanoyl]-L-prolinal | Rf 0.32 (EtOAc:CH$_3$OH = 9:1) | — |
| 2 (x) | 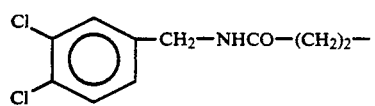 | N-[3-[N-(3,4-dichlorophenylmethyl)carbamoyl]-propanoyl]-L-prolinal | Rf 0.37 (EtOAc:CH$_3$OH = 9:1) | — |
| 2 (y) | 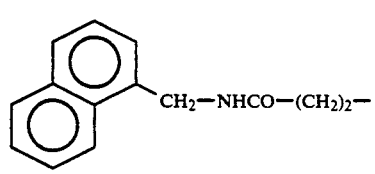 | N-[3-[N-(1-naphthylmethyl)carbamoyl]propanoyl]-L-prolinal | Rf 0.34 (EtOAc:CH$_3$OH = 9:1) | ν 3450, 3000, 1720, 1650–1620, 1500, 1430 |
| 2 (z) | 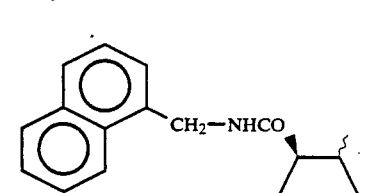 | N-[(1RS,2R)-2-[N-(1-naphthylmethyl)carbamoyl]cyclopentane-1-carbonyl]-L-prolinal | Rf 0.42 (EtOAc) | ν (KBr tablet) 3280, 1720, 1610, 1430, 770 |
| 2 (aa) | 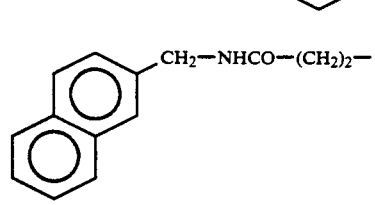 | N-[3-[N-(2-naphthylmethyl)carbamoyl]propanoyl]-L-prolinal | Rf 0.33 (EtOAc:CH$_3$OH = 9:1) | ν 1720, 1650, 1620, 1500, 1430 |
| 2 (bb) | 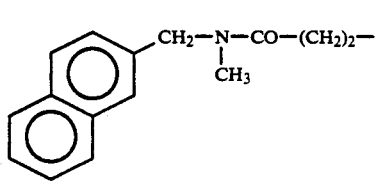 | N-[3-[N-methyl-N-(2-naphthylmethyl)carbamoyl]propanoyl]-L-prolinal | Rf 0.36 (EtOAc:CH$_3$OH = 9:1) | ν 3000–2880, 1710, 1650–1600, 1450–1400, 1110, 810, 740 |
| 2 (cc) | 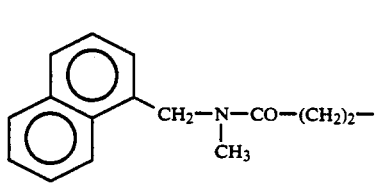 | N-[3-[N-methyl-N-(1-naphthylmethyl)carbamoyl]propanoyl]-L-prolinal | Rf 0.10 (EtOAc) | ν (CHCl$_3$ solution) 1725, 1630, 1430 |

TABLE III-continued

| No. | D—B—NR—CO—A— | Name | TLC | IR (cm$^{-1}$) |
|---|---|---|---|---|
| 2 (dd) | 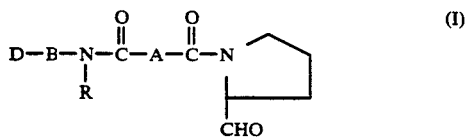 | N-[3-[N-(2-furyl-methyl)carbamoyl]propanoyl]-L-prolinal | Rf 0.34 (EtOAc:CH$_3$OH = 9:1) | $\nu$ (CHCl$_3$ solution) 3450, 3000, 1730, 1660–1620, 1500, 1430 |
| 2 (ee) | | N-[3-[N-(9-fluorenyl)carbamoyl]propanoyl]-L-prolinal | Rf 0.37 (EtOAc:CH$_3$OH = 9:1) | $\nu$ (KBr tablet) 3270, 1720, 1630, 1530, 1430, 760, 740 |

FORMULATION EXAMPLE

The following components were admixed in conventional method and punched out to obtain 100 tablets each containing 50 mg of active ingredient.

| | |
|---|---|
| N-[3-[N-(2-phenylethyl)carbamoyl]propanoyl]-L-prolinal | 5 g |
| Cellulose calcium gluconate (disintegrating agent) | 0.2 g |
| Magnesium stearate (lubricating agent) | 0.1 g |
| Microcrystalline cellulose | 4.7 g |

What is claimed is:

1. A novel prolinal derivative of the formula (I):

$$D-B-\underset{R}{N}-\overset{O}{\underset{\|}{C}}-A-\overset{O}{\underset{\|}{C}}-N\underset{CHO}{\diagup}\quad (I)$$

wherein A represents alkylene group of from 1 to 8 carbon atom(s) or alkenylene group of from 2 to 8 carbon atoms or a saturated hydrocarbon ring of from 3 to 7 carbon atoms, R represents hydrogen atom, phenyl group, benzyl group, alkyl group of from 1 to 8 carbon atom(s) or cycloalkyl group of from 3 to 7 carbon atoms, B represents a single bond or alkylene group of from 1 to 8 atom(s) unsubstituted or substituted by a phenyl group or a benzyl group, D represents a mono-nitrogen heterocyclic ring(s) containing not more than 15 ring members, which heterocyclic ring(s) are unsubstituted or substituted by from one to three of halogen atom, alkyl or alkoxy group of from 1 to 4 carbon atom(s) nitro group or trifluoromethyl group.

2. A compound according to claim 1, wherein D is pyridine or acridine ring which may be saturated partially and unsubstituted or substituted or fully saturated and unsubstituted or substituted, wherein the substituent(s) is/are from one to three of halogen atom, alkyl or alkoxy group of from 1 to 4 carbon atom(s), nitro group or trifluoromethyl group.

3. A compound according to claim 2, wherein D is, pyridine or partially saturated acridine ring which is unsubstituted.

4. A pharmaceutical composition for treating amnesia which comprises an effective amount of prolinal derivative of the formula (I) depicted in claim 1 and pharmaceutically acceptable carrier and/or coating.

5. The method for treating amnesia which comprises administering a therapeutically effective amount of prolinal derivative of the formula (I) depicted in claim 1.

6. The prolinal derivative according to claim 1, which is N-[3-[N-(4-pyridyl-methyl)carbamoyl]-propanoyl]-L-prolinal.

* * * * *